US012743784B2

(12) United States Patent
Gou et al.

(10) Patent No.: US 12,743,784 B2
(45) Date of Patent: Sep. 22, 2026

(54) MEDICAL IMAGE PROCESSING APPARATUS AND MEDICAL IMAGE PROCESSING METHOD

(71) Applicant: Canon Kabushiki Kaisha, Tokyo (JP)

(72) Inventors: Panjie Gou, Beijing (CN); Qilin Xiao, Beijing (CN); Hong Yang, Beijing (CN); Chunqi Wang, Beijing (CN); Shun Zhao, Beijing (CN)

(73) Assignee: Canon Kabushiki Kaisha, Tokyo (JP)

( * ) Notice: Subject to any disclaimer, the term of this patent is extended or adjusted under 35 U.S.C. 154(b) by 330 days.

(21) Appl. No.: 18/343,913

(22) Filed: Jun. 29, 2023

(65) Prior Publication Data

US 2024/0005513 A1 Jan. 4, 2024

(30) Foreign Application Priority Data

Jun. 29, 2022 (CN) ........................ 202210759465.X

(51) Int. Cl.

*G06T 7/12* (2017.01)
*G06T 7/00* (2017.01)
*G06V 10/25* (2022.01)
*G06V 10/44* (2022.01)
*G16H 30/40* (2018.01)

(52) U.S. Cl.

CPC .............. *G06T 7/12* (2017.01); *G06T 7/0012* (2013.01); *G06V 10/25* (2022.01); *G06V 10/44* (2022.01); *G16H 30/40* (2018.01); *G06T 2207/30081* (2013.01)

(58) Field of Classification Search

CPC ..................................................... G16H 30/40
See application file for complete search history.

(56) References Cited

U.S. PATENT DOCUMENTS 9,025,841 B2 5/2015 Wels et al.
9,269,156 B2 2/2016 Birkbeck et al.
9,536,316 B2 * 1/2017 Park .......................... G06T 7/11
2011/0116698 A1 5/2011 Weis et al.
2021/0383547 A1 * 12/2021 Lu ............................ G06T 7/11

FOREIGN PATENT DOCUMENTS

CN 107590808 A 1/2018

OTHER PUBLICATIONS

De Vos et al, "ConvNet-Based Localization of Anatomical Structures in 3-D Medical Images", IEEE, pp. 1470-1481, 2017 (Year: 2017).*

(Continued)

*Primary Examiner* — Edward Park
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to generate, from a medical image, a plurality of feature target regions for specifying a target of image segmentation. The processing circuitry is configured to specify a target region indicating the region in which the target is present, on a basis of the plurality of feature target regions. The processing circuitry is configured to perform, in the target region, the image segmentation on the target.

8 Claims, 9 Drawing Sheets

(56) References Cited

OTHER PUBLICATIONS

Hansis, et al, "Landmark constellation models for medical image content identification and localization", Int J Cars, pp. 1285-1295, 2015 (Year: 2015).*
Bagur et al, "Pancreas MRI Segmentation Into Head, Body, and Tail Enables Regional Quantitative Analysis of Heterogeneous Disease", pp. 997-1008, Feb. 2022 (Year: 2022).*
McEvoy et al, "Preoperative Prostate MRI: A Road Map for Surgery", Genitourinar y Imaging, pp. 383-391, 2018 (Year: 2018).*
Soberanis-Mukul, et al, "Uncertainty-based graph convolutional networks for organ segmentation refinement", ML, 2020, pp. 1-15 (Year: 2020).*
Office Action issued Mar. 27, 2026, in corresponding Chinese Patent Application No. 202210759465.X with English translation, citing documents 1 and 2 therein, 17 pages.

* cited by examiner

MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from Chinese Patent Application No. 202210759465.X, filed on Jun. 29, 2022, the entire contents of all of which are incorporated herein by reference.

FIELD

Embodiments described herein relate generally to a medical image processing apparatus and a medical image processing method.

More specifically, the present embodiments relate to the medical image processing apparatus and the medical image processing method for performing image segmentation by confirming a segmentation target region on the basis of a plurality of features points.

BACKGROUND

Image segmentation technology is one of key technology elements of medical image processing. By performing image segmentation on a specific organ or tissue in a medical image rendering an internal structure of a subject's body, contour information of the organ or the tissue is obtained.

Image segmentation plays an important role in clinical application. For example, in nuclear magnetic resonance imaging, it is necessary to specify the position of a target to be scanned ("scan target") in the subject's body and to further specify parameters such as a scan angle and an imaging reconstruction range (a Field Of View (FOV)). The process of setting those parameters increases workloads of operators and prolongs the time it takes to obtain a nuclear magnetic resonance image. To cope with this situation, by performing image segmentation on a nuclear magnetic resonance position determining image, it is possible to quickly determine the position in which the scan target is present, to further obtain information such as a scan angle, and to thereby realize a fully automatic scan.

For example, image segmentation performed on the prostate plays an important role in an ultrasound-guided prostate needle biopsy, ultrasound prostate image registration, and the like. For an ultrasound image-guided prostate needle biopsy, it is necessary to plan a puncture point position in advance in order to ensure that the puncture point is able to cover the entire region of the prostate. By performing the image segmentation on the prostate, it is possible to automatically specify the position in which the prostate is present, to save medical doctors the time to perform manual drawing, and to thus improve work efficiency. Further, the ultrasound prostate image registration is an important step in ultrasound-guided prostate ablation surgery. By accurately understanding the position in which the prostate is present, it is possible to eliminate invalid regions and to strengthen application to edge regions, which is greatly helpful for the prostate ultrasound/nuclear magnetic resonance image registration.

For example, a two-stage image segmentation method is known by which initial segmentation is at first performed on a pre-processed image, and subsequently, the boundary of a target organ obtained from the initial segmentation is finely adjusted so as to obtain a final target organ segmentation result. As another example, another image segmentation method is known by which image segmentation is performed by going through a series of detection steps while using a plurality of machine learning models.

DETAILED DESCRIPTION

Figure 1:
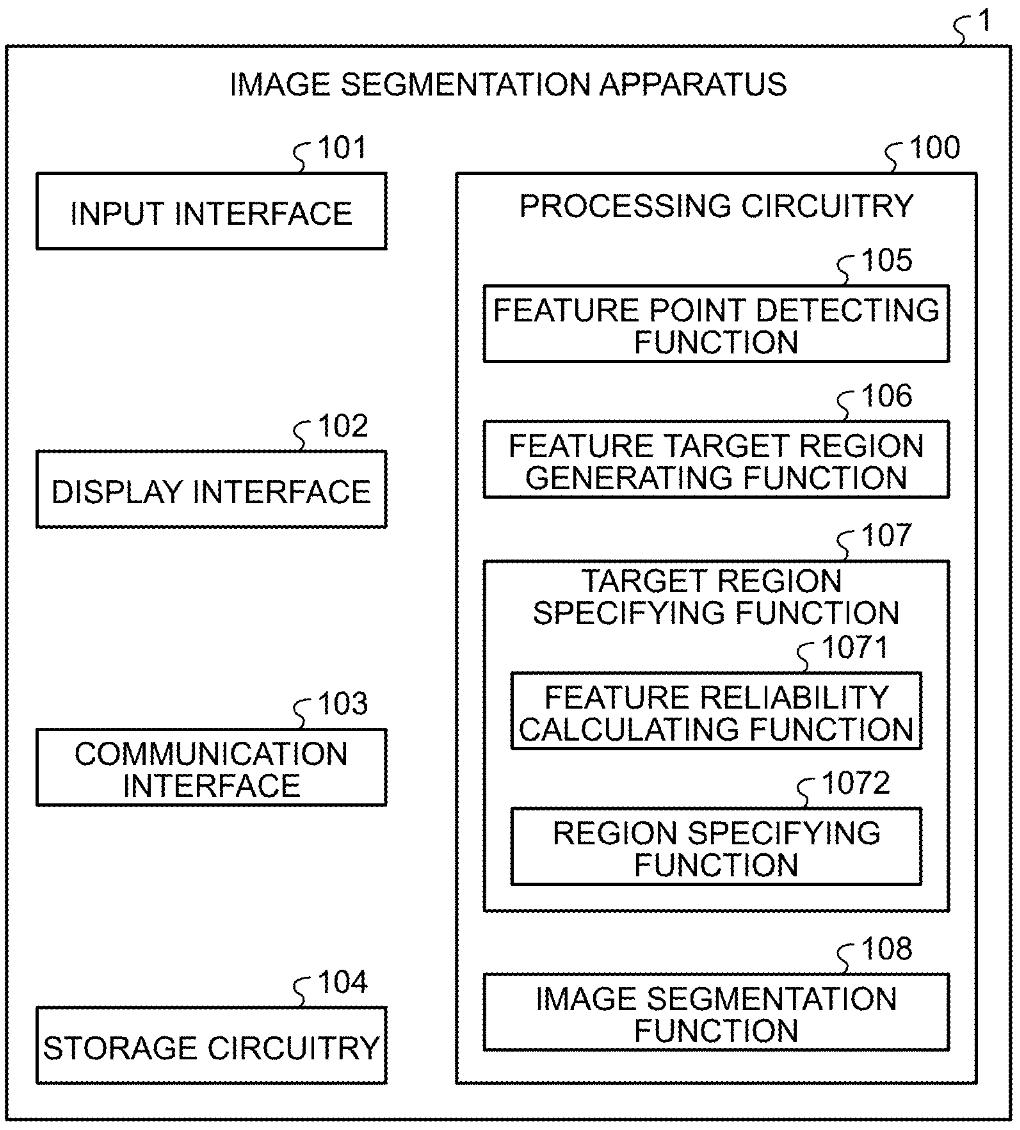
FIG. 1 is a diagram illustrating an exemplary configuration of an image segmentation apparatus according to an embodiment of the present disclosure.

According to an embodiment, a medical image processing apparatus comprises processing circuitry. The processing circuitry is configured to generate, from a medical image, a plurality of feature target regions for specifying a target of image segmentation. The processing circuitry is configured to specify a target region indicating the region in which the target is present, on a basis of the plurality of feature target regions. The processing circuitry is configured to perform, in the target region, the image segmentation on the target.

According to the image segmentation method described above by which the two-stage image segmentation is performed on the prostate, because pixel values of the prostate are close to pixel values of a bladder wall in the vicinity of the prostate, the initial segmentation is able to only roughly specify the position of the prostate. As a result, the initial segmentation may include many mis-segmented regions in some situations. In those situations, it is not possible to correct the mis-segmented regions even by making a fine adjustment on the boundary obtained from the initial segmentation, and the precision level of the segmentation may therefore be low. Further, according to the image segmentation method using a plurality of machine learning models, it is necessary to train each of the machine learning models, which requires a large volume of training data and a long training time. Further, there is a problem where if a detection mistake or a detection error occurs in one of the detection steps, the precision levels of the detection in the subsequent steps are impacted, which makes stability of the detection low.

To solve the problems described above, it is an object of the present disclosure to provide a medical image processing apparatus and a medical image processing method capable of easily and precisely performing image segmentation on a segmentation target while inhibiting occurrence of over-segmentation.

A medical image processing apparatus according to an embodiment of the present disclosure is a medical image processing apparatus that performs image segmentation on a target designated in a medical image and that includes: a feature point detecting function configured to detect, from the medical image, position information of a feature point for specifying a region in which the target is present; a feature target region generating function configured to generate a feature target region for specifying the region in which the target is present, on the basis of a positional relationship between the feature point and the target and to further bring the feature point into association with the feature target region; a target region specifying function configured to specify a target region indicating the region in which the target is present, on the basis of position information of a plurality of feature points including the feature point and information about a plurality of feature target regions including the feature target region and respectively associated with the plurality of feature points; and a segmentation unit configured to perform, in the target region, the image segmentation on the target.

A medical image processing method according to an embodiment of the present disclosure is a medical image processing method that is for performing image segmentation on a target designated in a medical image and that includes: a feature point detecting step of detecting, from the medical image, position information of a feature point for specifying a region in which the target is present; a feature target region generating step of generating a feature target region for specifying the region in which the target is present, on the basis of a positional relationship between the feature point and the target and further bringing the feature point into association with the feature target region; a target region specifying step of specifying a target region indicating the region in which the target is present, on the basis of position information of a plurality of feature points including the feature point and information about a plurality of feature target regions including the feature target region and respectively associated with the plurality of feature points; and a segmentation step of performing, in the target region, the image segmentation on the target.

Exemplary embodiments of a medical image processing apparatus and a medical image processing method of the present disclosure will be explained in detail below, with reference to the accompanying drawings. Possible embodiments of the medical image processing apparatus and the medical image processing method of the present disclosure are not limited to the embodiments described below. Further, in the following sections, an image segmentation apparatus will be explained as an example of the medical image processing apparatus.

An Image Segmentation Apparatus

FIG. 1 is a diagram illustrating an exemplary configuration of an image segmentation apparatus according to an embodiment of the present disclosure. An image segmentation apparatus 1 according to the present embodiment includes an input interface 101, a display interface 102, a communication interface 103, storage circuitry 104, and processing circuitry 100. The input interface 101, the display interface 102, the communication interface 103, the storage circuitry 104, and the processing circuitry 100 are connected so as to be able to communicate with one another.

The input interface 101 is configured to connect the image segmentation apparatus 1 to an input apparatus (not illustrated), to receive an operation of a user from the input apparatus, and to transfer a signal based on the received operation to the image segmentation apparatus 1. The input interface 101 is a serial bus interface such as a Universal Serial Bus (USB), for instance. Examples of the input apparatus include a mouse, a keyboard, a trackball, a switch, a button, a joystick, a touch screen, and a microphone. Further, the input interface 101 may be connected to a storage apparatus, so that various types of data are read from and written to the storage apparatus. The storage apparatus is, for example, a Hard Disc Drive (HDD), a Solid State Drive (SDD), or the like.

The display interface 102 is configured to connect the image segmentation apparatus 1 to a display apparatus (not illustrated) and to transmit data to the display apparatus so as to have an image displayed. The display interface 102 is a picture output interface such as a Digital Visual Interface (DVI) or a High-Definition Multimedia Interface (HDMI (registered trademark)), for example. Examples of the display apparatus include a Liquid Crystal Display (LCD) and an organic Electroluminescence (EL) display. The display apparatus is configured to display a user interface for receiving an input operation from the user, image data output by the image segmentation apparatus 1, and the like. Examples of the User Interface Include a Graphical User Interface (GUI).

The communication interface 103 is configured to connect the image segmentation apparatus 1 to a server (not illustrated) and is capable of transmitting and receiving various types of data to and from the server. For example, the communication interface 103 is a network card such as a wireless network card or a wired network card.

The storage circuitry 104 is configured to store therein a medical image for performing image segmentation and a result of the image segmentation. Further, the storage circuitry 104 is configured to store therein parameters of a machine learning model used by the image segmentation apparatus 1, e.g., parameters of the machine learning model used by a feature point detecting function 105 and an image segmentation function 108 (explained later). The storage circuitry 104 is realized by using a storage apparatus such as a Read-Only Memory (ROM), a flash memory, a Random Access Memory (RAM), a Hard Disc Drive (HDD), an SSD, or a register, for example. The flash memory, the HDD, and the SSD are each a non-volatile storage medium. It is possible to realize any of these non-volatile storage media by using another storage apparatus connected via a network, such as a Network Attached Storage or an external storage server apparatus. In this situation, examples of the network include the Internet, a Wide Area Network (WAN), a Local Area Network (LAN), a carrier terminal, a wireless communication network, a wireless base station, and a dedicated communication line.

As illustrated in FIG. 1, the processing circuitry 100 is configured to execute the feature point detecting function 105, a feature target region generating function 106, a target region specifying function 107, and the image segmentation function 108. The processing circuitry 100 is realized by using a processor, for example. In that situation, in that situation, the abovementioned processing functions are stored in the storage circuitry 104 in the form of computer-executable programs. Further, the processing circuitry 100 is configured to realize the functions corresponding to the programs, by reading and executing the programs stored in the storage circuitry 104. In other words, the processing circuitry 100 that has read the programs has the processing functions illustrated in FIG. 1.

The feature point detecting function 105 is configured, by employing a trained machine learning model, to detect, from a medical image, position information of a feature point for specifying a region in which a target subject to segmentation (hereinafter, "segmentation target") is present and configured to output the position of the feature point in the image and a feature point position reliability coefficient.

Selected as the feature point is a point that is positioned inside or in the surroundings of the segmentation target, has a prominent anatomical feature, and has a relatively stable relative positional relationship with the segmentation target. It is desirable to use, as the feature point, a point of which the machine learning model is able to precisely determine the position. In this situation, the prominent anatomical feature denotes a feature that can easily be distinguished from the other parts in the medical image. The relative positional relationship being stable means that the positional relationship between the feature point and the segmentation target does not widely vary dependent on individual differences among examined subjects. The feature point position reliability coefficient is a coefficient indicating reliability of the detected position of the feature point and is proportional to a probability of whether or not the detected position is accurate. The machine learning model or a deep learning model may be configured to output the feature point position reliability coefficient, in addition to outputting the position of the feature point. It is desirable when the feature point position reliability coefficient is a probability indicating whether or not the detected position is accurate.

In an example, two or more feature points may be provided. For example, when the segmentation target is the prostate, a prostate center point and a prostate apex point or the like may be provided as points inside the segmentation target, whereas femur points on the left and the right and a urethra entrance point or the like may be provided as points in the vicinity of the segmentation target. When two or more feature points are provided, it is acceptable to provide a different machine learning model for each of the feature points. Alternatively, it is also acceptable to use a single machine learning model, so as to output the positions and feature point position reliability coefficients of the feature points through mutually-different output layers. As the machine learning model, it is possible to use a model based on a Hough Forest detection algorithm or a deep learning model based on a neural network. As the deep learning model, preferably a model based on a convolutional neural network may be used, and more preferably, an hourglass-based model may be used. When a neural network is used, models for mutually-different feature points may share an input layer and a plurality of neural network intermediate layers connected to the input layer, while having mutually-different output layers.

The feature target region generating function 106 is configured to generate, from a medical image, a plurality of feature target regions for specifying a target of image segmentation. More specifically, the feature target region generating function 106 is configured to generate a feature target region for specifying the region in which the segmentation target is present, on the basis of the positional relationship between the feature point detected by the feature point detecting function 105 and the segmentation target and to bring the generated feature target region into association with the feature point.

The feature target region generating function 106 is configured to estimate, as the feature target region, an approximate region in which the segmentation target is present, on the basis of the position of the feature point within the image and the relative positional relationship between the feature point and the segmentation target. For example, by determining, in advance, a relative positional relationship within the image between the center point of the segmentation target and the feature point while using a statistical method, the feature target region generating function 106 is configured to specify the position of the center point of the segmentation target on the basis of the detected position of the feature point and to subsequently confirm the feature target region on the basis of the center point of the segmentation target and the size and the shape of the segmentation target. In another example, the position of the feature target region may be determined on the basis of a plurality of feature points of which the positions are relevant to one another. More specifically, the position of the feature target region may be confirmed, further on the basis of a line connecting together the plurality of feature points or the center of the plurality of feature points. For example, when the segmentation target is the prostate, the feature target region generating function 106 may determine the position of the feature target region on the basis of femur points on the left and the right or a set of points on the pelvis.

In this situation, the feature target region is a region matching an outline of the segmentation target and may have an arbitrary three-dimensional shape. Preferably, the feature target region has a regular shape, and more preferably, the feature target region has a cuboid shape. It is possible to set the size of the feature target region as appropriate, in accordance with the age, the gender, the height, the weight, and/or the like of an examined subject to be scanned. The feature target region generating function 106 is configured to set the shape and the size of the feature target region so that the contour of the feature target region matches the outline of the segmentation target as much as possible.

The target region specifying function 107 is configured to specify a target region indicating the region in which the target is present, on a basis of the plurality of feature target regions. More specifically, the target region specifying function 107 is configured to specify the position of a target region in which the segmentation target is present, on the basis of the position information of the feature point detected by the feature point detecting function 105 and information about the feature target region generated by the feature target region generating function 106. For example, as illustrated in FIG. 1, the target region specifying function 107 includes a feature reliability calculating function 1071 and a region specifying function 1072.

The feature reliability calculating function 1071 is configured to calculate a degree of feature reliability (hereinafter, "feature reliability degree") with respect to the point at each of various positions within the image, on the basis of the feature point position reliability coefficient of the feature point and the feature target region associated therewith and to further bring data indicating the calculated feature reliability degrees of the positions into association with the feature point and the feature target region. In this situation, each of the feature reliability degrees expresses a probability that the position in the image specified from the specific feature point and the feature target region will belong to the target region. Thus, there is a possibility that a point in the same position within the image may have mutually-different feature reliability degrees, if being specified from mutually-different feature points and feature target regions. A method for calculating the feature reliability degrees will be explained later.

With respect to each of the points in the medical image, the region specifying function 1072 is configured to calculate a total reliability degree on the basis of the plurality of feature reliability degrees corresponding to the point and configured to further specify the target region, on the basis of one or more points of which the total reliability degrees are larger than a predetermined threshold value.

The image segmentation function 108 is configured to perform the image segmentation on the segmentation target within the target region of the medical image. It is possible to perform the image segmentation by using one of various known techniques. For example, the image segmentation may be performed by using a deep learning model based on a Convolutional Neural Network (CNN). It is preferable to perform the image segmentation by using a deep learning model based on U-Net.

An Image Segmentation Method

Figure 2:
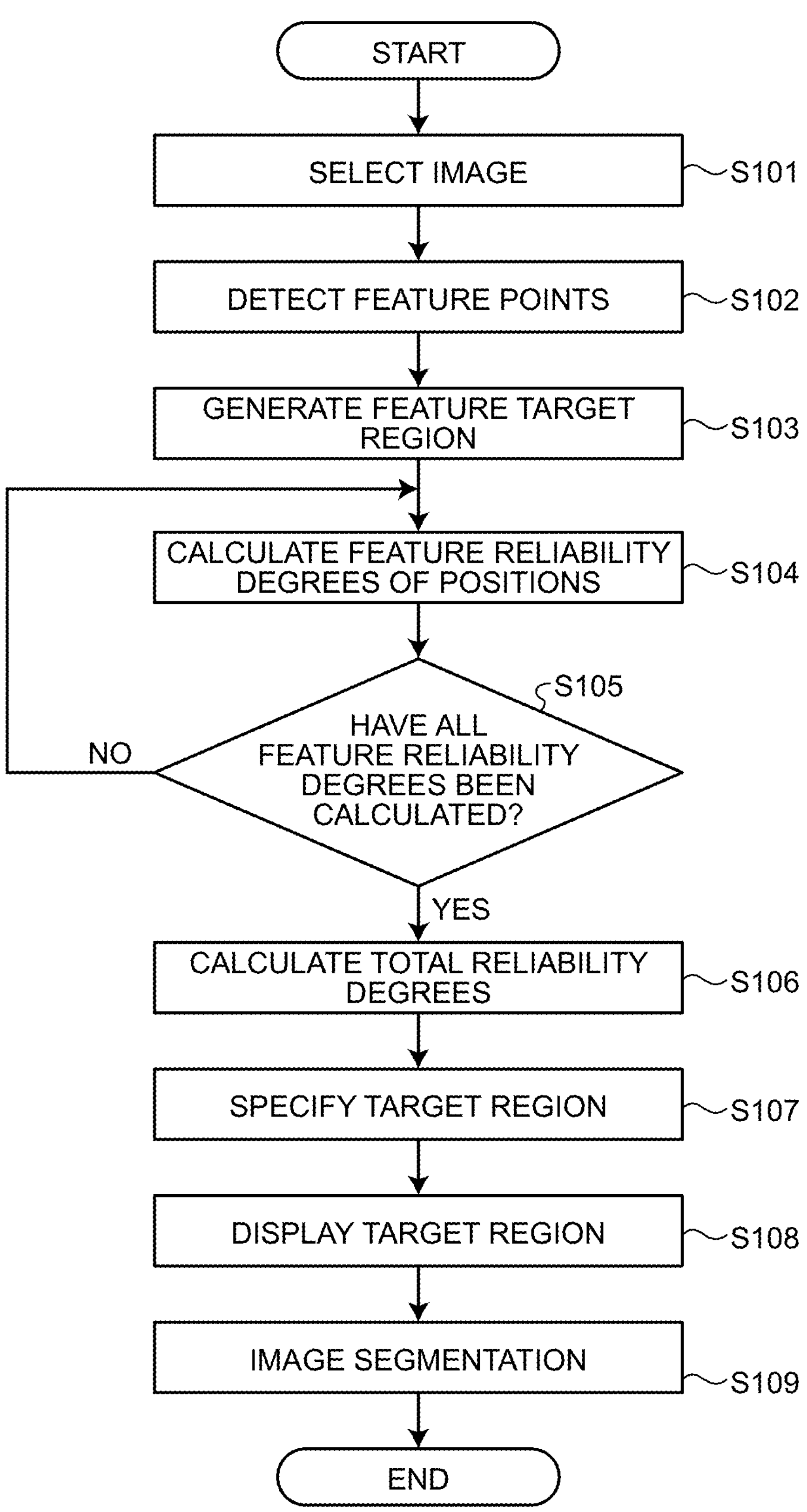
FIG. 2 is a flowchart illustrating an image segmentation method implemented on the prostate by the image segmentation apparatus according to the present embodiment.

FIG. 2 is a flowchart illustrating an image segmentation method implemented on the prostate by the image segmentation apparatus 1 according to the present embodiment. In the following sections, a procedure of performing the image segmentation on the prostate by using the image segmentation apparatus 1 according to the embodiment will be explained with reference to FIG. 2.

At step S101, from the storage circuitry 104, the user selects a medical image rendering the prostate on which the image segmentation needs to be performed as a target image and generates an image coordinate system. The image coordinate system is a three-dimensional orthogonal coordinate system generated from the medical image. Each of the points in the medical image corresponds to a set of coordinates in the image coordinate system in one-to-one correspondence.

In this situation, the medical image rendering the prostate is obtained by scanning a prostate region of the subject, by using an imaging technique such as Computed Tomography (CT) imaging, ultrasound imaging, or nuclear Magnetic Resonance Imaging (MRI), for example. The medical image rendering the prostate includes anatomical information of the prostate of the subject and indicates the structure of the prostate of the subject.

In the present embodiment, as the medical image rendering the prostate, a three-dimensional grayscale image having a width W×a height H×and a depth D. Each of the voxels in the medical image expresses structure information at a specific position within the prostate of the subject by using a grayscale scheme. The width direction, the height direction, and the depth direction of the medical image rendering the prostate correspond to the left-and-right direction, the up-and-down direction, and the front-and-back direction of the subject, respectively. The position of each of the voxels in the medical image rendering the prostate is expressed by using an orthogonal coordinate system defined by an X-axis, a Y-axis, and a Z-axis orthogonal to one another. In this situation, for example, the X-axis, the Y-axis, and the Z-axis correspond to the width direction, the height direction, and the depth direction of the image, respectively. In the following explanations, the X-axis positive direction corresponds to the left side of the subject; the X-axis negative direction corresponds to the right side of the subject; the Y-axis positive direction corresponds to the front side of the subject; the Y-axis negative direction corresponds to the rear side of the subject, the Z-axis positive direction corresponds to the top side of the subject, and the Z-axis negative direction corresponds to the bottom side of the subject. Alternatively, the medical image rendering the prostate may be a two-dimensional image or may be a Red-Green-Blue (RGB) color image.

At step S102, by using the trained machine learning model, the feature point detecting function 105 detects, within the image coordinate system, the positions of the plurality of prostate feature points in the target image and further calculates the feature point position reliability coefficients of the prostate feature points. For example, the feature point detecting function 105 detects, from the medical image, position information of a plurality of feature points including at least a first feature point and a second feature point.

In the present embodiment, detected as the feature points are: one pubic bone point, two femur points, four pelvis points, one urethra entrance point, one prostate center point, and one prostate apex point. In the following sections, a relative positional relationship between the feature points and the prostate will be explained, with reference to FIG. 3A to 3F.

Figure 3A:
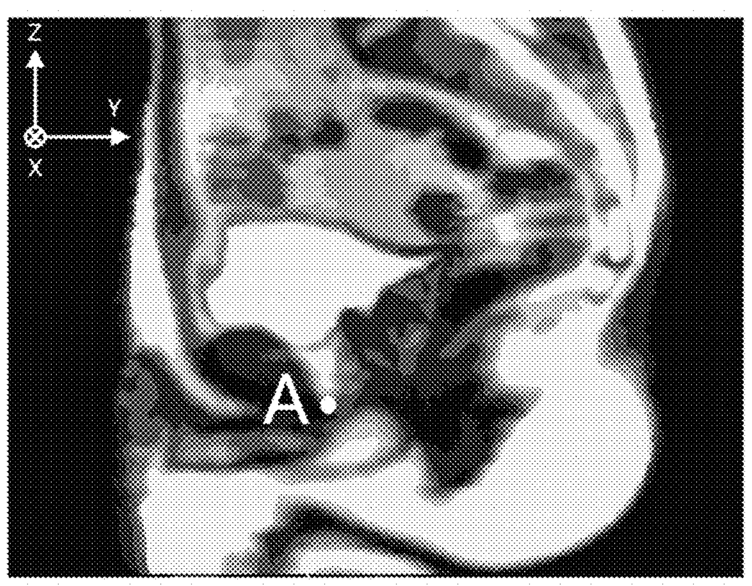
FIG. 3A is a drawing for explaining prostate feature points in image segmentation performed on the prostate by the image segmentation apparatus according to the present embodiment.

FIG. 3A is a sagittal cross-sectional view indicating relative positions between the pubic bone point and the prostate. In FIG. 3A, point A indicates the detected position of the pubic bone point. Because the pubic bone point is positioned below the prostate and has a prominent grayscale characteristic, the precision level for detecting the pubic bone point is high, and it is therefore possible to determine the position of a lower part of the prostate relatively accurately.

Figure 3B:
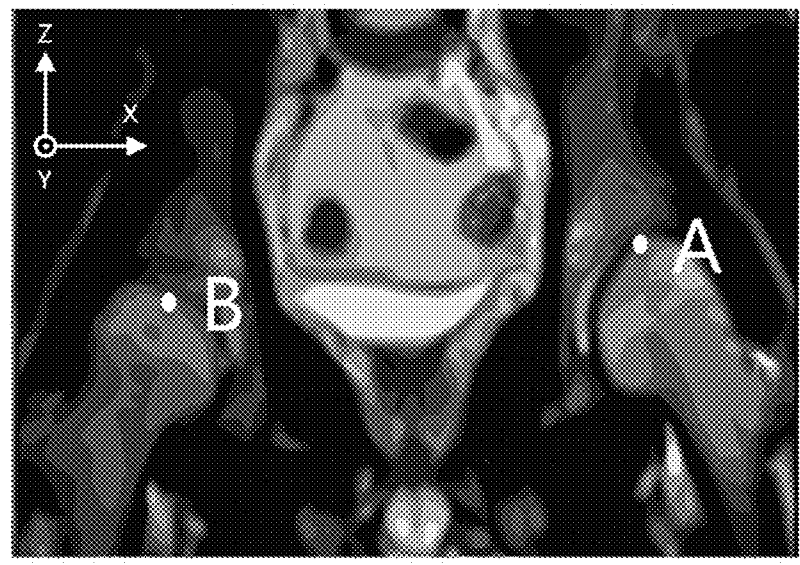
FIG. 3B is a drawing for explaining other prostate feature points in image segmentation performed on the prostate by the image segmentation apparatus according to the present embodiment.

FIG. 3B is a coronal cross-sectional view indicating relative positions between the two femur points and the prostate. In FIG. 3B, point A indicates the detected position of the left femur point, whereas point B indicates the detected position of the right femur point. Because the femur points are positioned on either side of the prostate and have prominent anatomical structures, the precision level for detecting the femur points is relatively high, and it is therefore possible to determine the left-and-right position of the prostate.

Figure 3C:
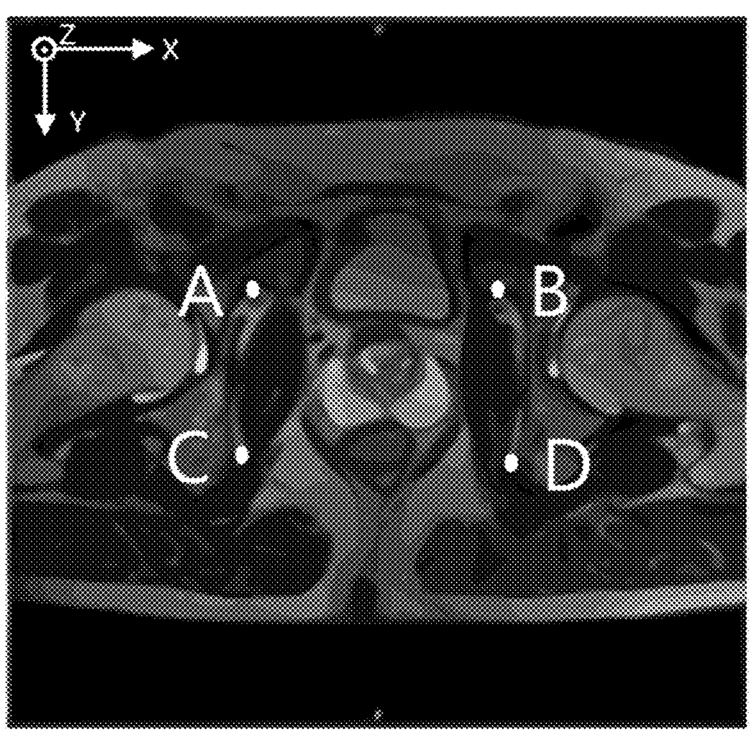
FIG. 3C is a drawing for explaining another prostate feature points in the image segmentation performed on the prostate by the image segmentation apparatus according to the present embodiment.

FIG. 3C is a horizontal cross-sectional view indicating relative positions between the four pelvis points and the prostate. In FIG. 3C, the four points, namely A, B, C, and D, indicate the detected positions of the four pelvis points, respectively. Because the pelvis is positioned in the surroundings of the prostate so as to surround a region in which the prostate is present, the precision level for detecting the pelvis points is relatively high, and it is therefore possible to determine the position of an outer edge of the prostate.

Figure 3D:
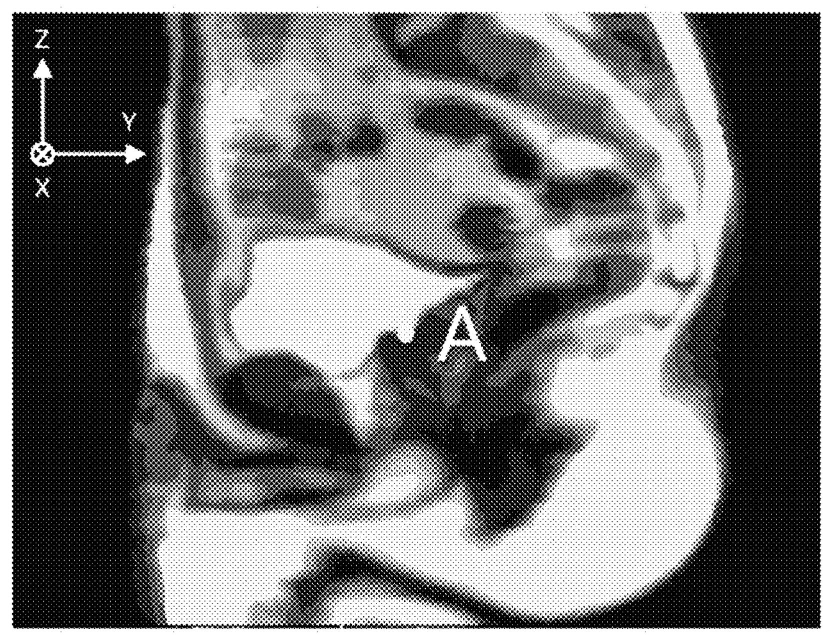
FIG. 3D is a drawing for explaining yet another prostate feature point in the image segmentation performed on the prostate by the image segmentation apparatus according to the present embodiment.

FIG. 3D is a sagittal cross-sectional view indicating relative positions between the urethra entrance point and the prostate. In FIG. 3D, point A indicates the detected position of the urethra entrance point. Because the urethra entrance point is positioned to the upper front of the prostate at the border between the bladder and the prostate, and the degree of difficulty for detecting urethra entrance point is high, the precision level for detecting the urethra entrance point is relatively low. The urethra entrance point is therefore possible to assist determining the position of an upper front part of the prostate.

Figure 3E:
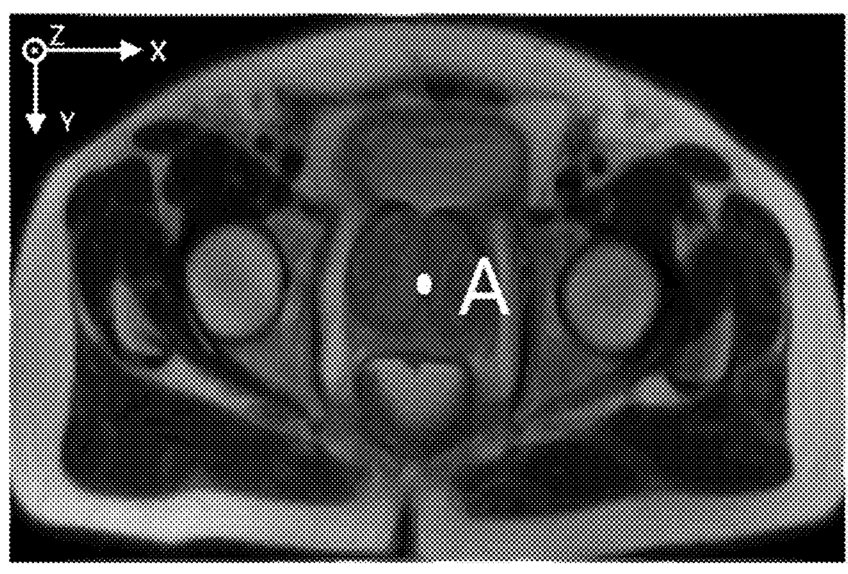
FIG. 3E is a drawing for explaining yet another prostate feature points in the image segmentation performed on the prostate by the image segmentation apparatus according to the present embodiment.

FIG. 3E is a horizontal cross-sectional view indicating relative positions between the prostate center point and the prostate. In FIG. 3E, point A indicates the detected position of the prostate center point. Because of being positioned at the exact center of the prostate, the prostate center point is possible to assist determining the position of the prostate region.

Figure 3F:
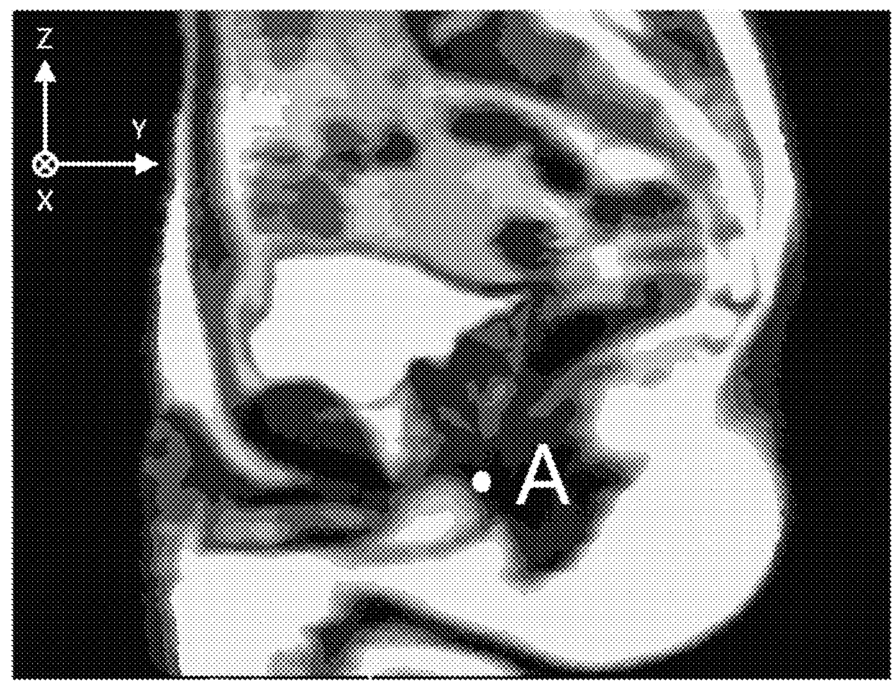
FIG. 3F is a drawing for explaining yet another prostate feature points in the image segmentation performed on the prostate by the image segmentation apparatus according to the present embodiment.

FIG. 3F is a sagittal cross-sectional view indicating relative positions between the prostate apex point and the prostate. In FIG. 3F, point A indicates the detected position of the prostate apex point. Because the prostate apex point is positioned in an apex part of the prostate, and the degree of difficulty for detecting the prostate apex point is high, the precision level for detecting the prostate apex point is relatively low. The prostate apex point is therefore possible to assist determining the up-and-down position of the prostate.

In the present embodiment, the positions of the feature points are detected by using the hourglass-based neural network, and the feature point position reliability coefficients of the feature points are calculated. The hourglass-based neural network may have an input layer corresponding to the size of the target image, a plurality of intermediate layers used in common, and an output layer corresponding to each of the feature points.

Next, an application method and a training method of the hourglass-based neural network will be explained.

To detect the feature points by using the hourglass-based neural network, the feature point detecting function 105 at first reads data representing the target image from the storage circuitry 104 and inputs the data to the input layer of the neural network. Subsequently, by performing a feed-forward process, the feature point detecting function 105 is configured to obtain, through the output layer corresponding to each of the plurality of feature points, data indicating a probability that the feature point corresponding to the output layer will be positioned at each set of coordinates in the image coordinate system. Further, with respect to each of the piece of data output by the output layers, the feature point detecting function 105 is configured to select the coordinates having the highest probability as the position of the feature point corresponding to the output layer and to further output the probability as the feature point position reliability coefficient.

At the time of training the hourglass-based neural network, at first, a plurality of sets of training data stored in advance are read from the storage circuitry 104. Each of the sets of training data includes a medical image rendering the prostate and serving as input data and data that corresponds to a different one of the plurality of feature points and indicates the actual position of the feature point.

After that, the plurality of sets of training data are divided into training sets and test sets. Examples of the ratio between the training sets and the test sets include 80% to 20% and 90% to 10%. For example, when there are 10,000 sets of training data in total, among the training data numbered Data #1 through #10,000, the data numbered Data #1 through #8,000 are assigned to be the training sets, whereas the data numbered Data #8,001 through #10,000 are assigned to be the test sets.

After that, from among the training sets, a predetermined number of pieces of data are randomly selected as one training batch. Input data extracted from the sets of training data in the training batch is input to the neural network. By performing a feed-forward process, the output layer corresponding to each of the plurality of feature points outputs data indicating a probability that the feature point corresponding to the output layer in the medical image rendering the prostate will be positioned at each set of coordinates in the image coordinate system. Subsequently, with respect to each input data, a set of coordinates having the highest probability is selected as the position of the feature point corresponding to the output layer, from the pieces of data output by the output layer. Further, a total difference value is calculated between predicted positions and the actual positions with respect to all the feature points in the present training batch. By performing a feed-backward process using a gradient descent algorithm or the like on the basis of the total difference value, the parameters of the neural networks are changed so as to minimize the difference values between the predicted positions and the actual positions of the feature points output by the neural network. Examples of the difference values that may be used include cross entropy values and mean squared errors. After the feed-forward process and the feed-backward process are performed as many times as a predetermined quantity of the training batches, a predetermined number of pieces of data in the test sets are randomly selected as one test batch. Input data extracted from the sets of training data in the test batch is input to the neural network. By performing a feed-forward process, the output layer corresponding to each of the plurality of feature points obtains the position of the feature point predicted by the neural network. Further, a total difference value is calculated between predicted positions and the actual positions with respect to all the feature points in the present test batch. It is then judged whether or not the difference value is smaller than a threshold value set in advance. When the difference value is smaller than the threshold value set in advance, it is determined that the training has completed. Otherwise, the training of the neural network is continued.

At step S103, in accordance with the types of the feature points, the feature target region generating function 106 generates a feature target region corresponding to each type of feature points in the image coordinate system, on the basis of the relative positional relationships between the feature points and the segmentation target and further brings the feature target region into association with each type of feature points. For example, the feature target region generating function 106 generates a first feature target region based on the first feature point and generate a second feature target region based on the second feature point.

Figure 4:
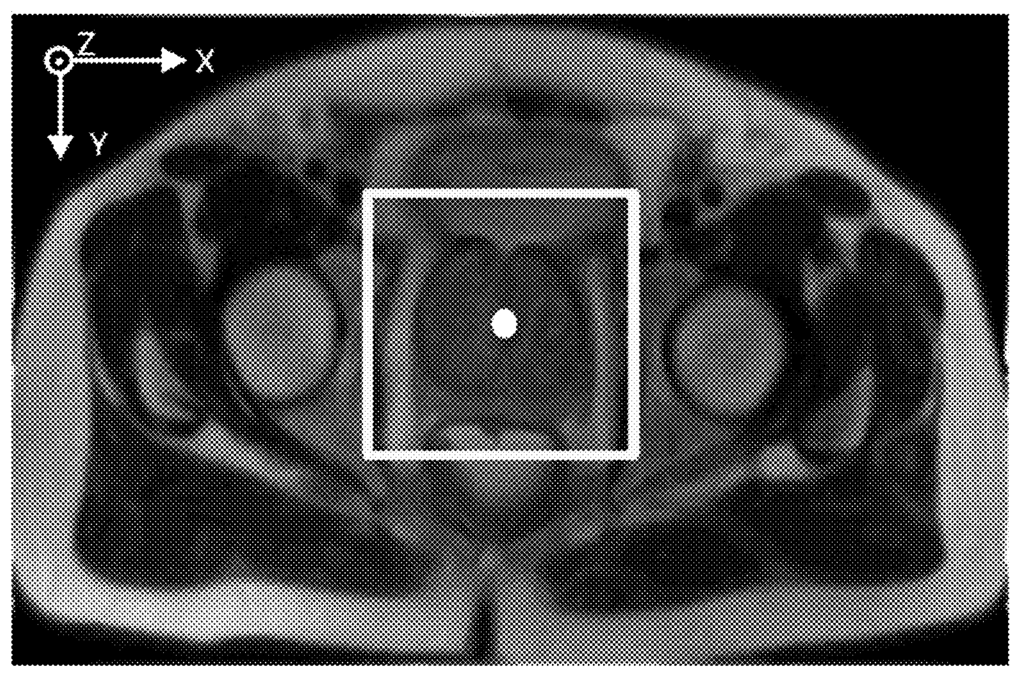
FIG. 4 is a horizontal cross-sectional view indicating the position of a feature target region specified on the basis of a prostate center point.
Figure 5:
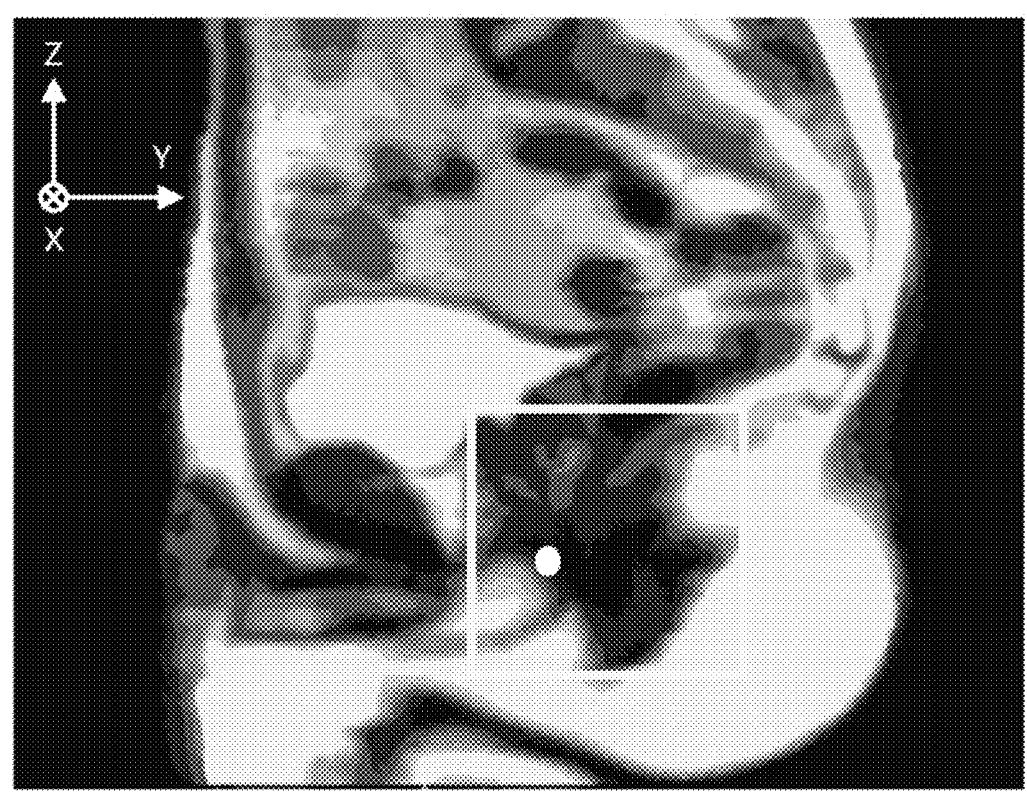
FIG. 5 is a sagittal cross-sectional view indicating the position of a feature target region specified on the basis of a prostate apex point.

When the feature point of a certain type includes only one feature point, the feature target region generating function 106 is configured to confirm the position of a feature target region on the basis of the relative positional relationship between the feature point and the prostate. Next, the process of confirming the feature target region will be explained, with reference to drawings. FIG. 4 is a horizontal cross-sectional view indicating the position of the feature target region confirmed on the basis of the prostate center point. As illustrated in FIG. 4, the prostate center point is positioned at the exact center of the prostate. Thus, the feature target region generating function 106 determines a cubic region extending 50 mm above and below, 50 mm to the left and to the right, and 50 mm to the front and to the rear of the prostate center point, as a feature target region associated with the prostate center point. FIG. 5 is a sagittal cross-sectional view indicating the position of the feature target region confirmed on the basis of the prostate apex point. As illustrated in FIG. 5, because the prostate apex point is positioned at the apex part of the prostate, the feature target region generating function 106 determines a cubic region extending 40 mm above, mm below, 50 mm to the left and to the right, 70 mm to the front, and 30 mm to the rear of the prostate apex point, as a feature target region associated with the prostate apex point.

Further, when the feature points of a certain type include a plurality of feature points, the feature target region generating function 106 confirms the position of a feature target region on the basis of, not only the relative positional relationship between the plurality of feature points and the prostate, but also lines connecting the plurality of feature points together and the position of an intersecting point of the connecting lines, or the like. For example, because the femur points are positioned above the prostate, the feature target region generating function 106 is able to determine the left boundary of a feature target region to be 30 mm to the right of the left femur point, the right boundary thereof to be 30 mm to the left of the right femur point, the top boundary thereof to be a line connecting together the two femur points, the bottom boundary to be 100 mm below the line connecting together the two femur points, and the front and the rear boundaries to be 50 mm to the front and to the rear of the line connecting together the two femur points.

Next, the target region specifying function 107 specifies the target region, on a basis of the first feature target region and the second feature target region. More specifically, at step S104, the feature reliability calculating function 1071 of the target region specifying function 107 calculates a feature reliability degree of a point at each of the various positions in the target image, on the basis of the position information of the one or more feature points of a certain type and the information about the feature target region associated with the one or more feature points of the particular type and further brings the data indicating the calculated feature reliability degrees of the points into association with the one or more feature points of the particular type and the feature target region.

More specifically, at first, the feature reliability calculating function 1071 reads, from the storage circuitry 104, the feature point position reliability coefficient of the feature point of a certain type of which the feature reliability degree has not yet been calculated and information about the feature target region associated with the feature point of the particular type. In the present embodiment, the feature point position reliability coefficient is the probability that was output from the neural network at step S102 and indicates that the detected position of the feature point is accurate. After that, with respect to each of the various points in the image, the feature reliability calculating function 1071 calculates the distance to a boundary of the feature target region positioned closest to the point. More specifically, with respect to each of the various points in the image, the feature reliability calculating function 1071 calculates, in the image coordinate system, a vertical distance in the millimeter unit between the coordinates of the point and each of the boundary planes of the feature target region and further selects the shortest one of the calculated distances as the distance to a boundary of the feature target region positioned closest to the point. After that, by using Expression (1) presented below, the feature reliability calculating function 1071 calculates a feature reliability degree of each of the various points in the target image.

$$f = \frac{1}{1 + e^{conf \cdot dist \cdot flag}} \tag{1}$$

In Expression (1), "f" denotes the feature reliability degree, while "conf" denotes the feature point position reliability coefficient of the feature point, "dist" denotes the distance to a boundary of the feature target region positioned closest the point, and "flag" denotes a flag indicating whether or not the coordinates of the point belong to the feature region. The value of the flag is "−1" when the point is positioned inside the feature region, whereas the value of the flag is "1" when the point is positioned outside the feature region.

Further, the feature reliability calculating function 1071 brings the data indicating the calculated feature reliability degrees of the points into association with the feature point of the particular type and the feature target region.

According to Expression (1), the more distant a point inside the feature target region is from the closest boundary of the feature target region, i.e., the closer the point is to a center region of the feature target region, the higher is the feature reliability degree of the point. In contrast, the closer a point inside the feature target region is to the closest boundary of the feature target region, i.e., the closer the point is to the boundary of the feature target region, the lower is the feature reliability degree of the point. On the contrary, the more distant a point outside the feature target region is from the closest boundary of the feature target region, i.e., the more distant the point is from the feature target region, the lower is the feature reliability degree of the point. In contrast, the closer a point outside the feature target region is to the closest boundary of the feature target region, i.e., the closer the point is to the feature target region, the higher is the feature reliability degree of the point. The maximum value of the feature reliability degree of a point inside the feature target region is 1, in which case it is ascertained that the point belongs to the prostate region on the basis of the feature point of the particular type and the feature target region. The minimum value of the feature reliability degree of a point inside the feature target region is 0.5, in which case it cannot be ascertained whether or not the point belongs to the prostate region on the basis of the feature point of the particular type and the feature target region. The minimum value of the feature reliability degree of a point outside the feature target region is 0, in which case it is ascertained that the point does not belong to the prostate region on the basis of the feature point of the particular type and the feature target region. The maximum value of the feature reliability degree of a point outside the feature target region is 0.5, in which case it cannot be ascertained whether or not the point belongs to the prostate region on the basis of the feature point of the particular type and the feature target region.

Figure 6:
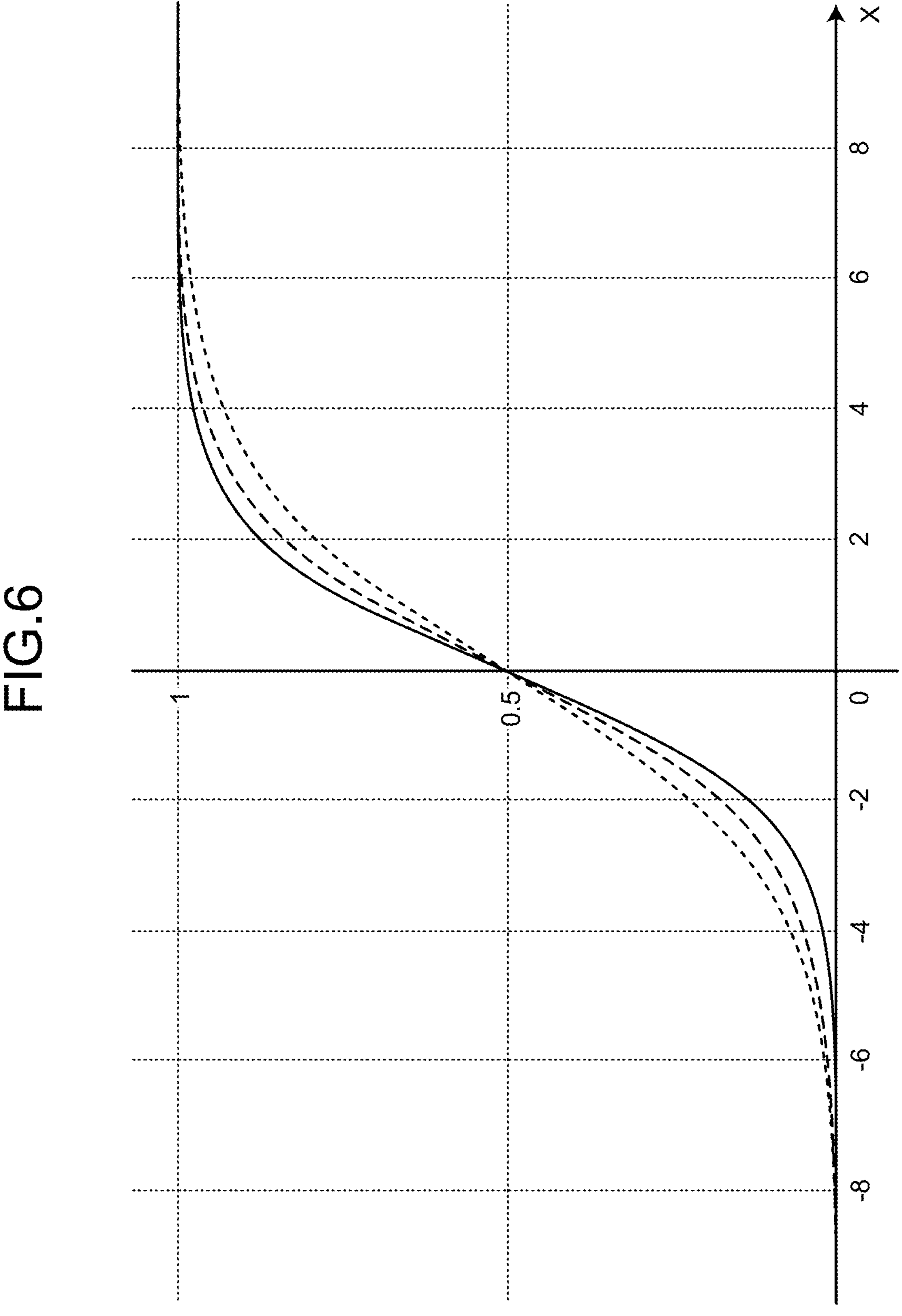
FIG. 6 is a feature reliability distribution chart corresponding to various feature point position reliability coefficients.

FIG. 6 is a feature reliability distribution chart corresponding to various feature point position reliability coefficients. In FIG. 6, the horizontal axis expresses distances to a boundary of the feature target region positioned closest to the coordinates of the point. The vertical axis expresses feature reliability degrees. The solid line indicates a feature reliability distribution corresponding to a feature point of which the feature point position reliability coefficient is 0.95. The dashed line indicates a feature reliability distribution corresponding to a feature point of which the feature point position reliability coefficient is 0.8. The dotted line indicates a feature reliability distribution corresponding to a feature point of which the feature point position reliability coefficient is 0.65. As illustrated in FIG. 6, the larger the feature point position reliability coefficient is, the higher is the feature reliability degree of each of the points in the target image, and the wider is the range distribution of the points closer to 1. Conversely, the smaller the feature point position reliability coefficient is, the lower is the feature reliability degree of each of the points in the target image, and the narrower is the range distribution of the points closer to 1.

In the present embodiment, because the feature reliability degrees are calculated from the feature point position reliability coefficients, it is possible to inhibit erroneous detections of the neural network and errors caused by noise. Further, because the feature reliability degrees are calculated on the basis of the relative positions between the points in the target image and the feature target region, it is possible to sufficiently utilize the anatomical information included in the target image and to thus improve the precision levels of the feature reliability degrees.

At step S105, the target region specifying function 107 judges whether or not the feature reliability degrees have been calculated with respect to the feature points of all the types and the feature target regions associated with the feature points. When the judgment result is "Yes", the process proceeds to step S106. When the judgment result is "No", the process returns to step S104, where the calculation of the feature reliability degrees is continued.

At step S106, the region specifying function 1072 of the target region specifying function 107 calculates, with respect to each of the various points in the target image, a total reliability degree by using Expression (2) presented below, on the basis of all the feature reliability degrees associated with the point.

$$F = \sum_{i=1}^{N} w_i \cdot f_i \qquad (2)$$

In Expression (2), "F" denotes the total reliability degree; "wi" denotes a weight on a feature point of an i-th type; "fi" denotes a feature reliability degree of a point calculated on the basis of the feature point of the i-th type and the feature target region by using Expression (1); and "N" denotes the total quantity of the types of the feature points. The reliability varies among the different types of feature points. For example, the pubic bone point is always conspicuous in medical images and is detected more easily, whereas the urethra entrance point is relatively more difficult to be detected. Thus, larger weights are applied to feature points having higher detection reliability, and smaller weights are applied to feature points having lower detection reliability. Further, the weights are calculated while stability of the detected points themselves is taken into account. In other words, larger weights are applied to detected points that are less easily impacted by individual differences, whereas smaller weights are applied to feature points of which detection results can have larger variances. In the present embodiment, the weights on the pubic bone point, the femur points, the pelvis points, the urethra entrance point, the prostate center point, and the prostate apex point are set to 1.0. 0.7, 0.7, 0.5, 0.7, and 0.5, respectively.

At step S107, the region specifying function 1072 specifies the positions of all the points of which the total reliability degree is larger than a threshold value set in advance and determines a minimum bounding cuboid of the region structured by these points as a prostate region. Further, upon determining that the target region detection has failed, e.g., when the quantity of the points of which the total reliability degrees are larger than the threshold value set in advance is too small, or when the volume of the minimum bounding cuboid is too small, the region specifying function 1072 determines a region being centered on the prostate center point and extending 50 mm above and below, 50 mm to the left and to the right, and 50 mm to the front and to the rear, as a prostate region.

At step S108, the target region specifying function 107 causes a display apparatus to display the target image and the prostate region specified at step S107.

At step S109, the image segmentation function 108 performs the image segmentation on the prostate within the specified prostate region, on the basis of the target image. It is possible to perform the image segmentation by using one of various known techniques. It is preferable to use a deep learning model structured with a convolutional neural network including an input layer, an output layer, a convolution layer, an activation layer, a pooling layer, a batch normalization layer, and a fully connected layer. It is more preferable to use a deep learning model based on 2D-UNet.

In the present embodiment, because the target region is specified on the basis of the position information of the plurality of feature points, even when one of the feature points deviates from the position due to an individual difference of the subject, it is possible to determine the position of the prostate with certainty. Further, because the weights are applied to the feature reliability degrees in accordance with the reliability and the stability of the feature points, it is possible to further improve the reliability of the specified prostate region.

Advantageous Technical Effects

Next, an image segmentation method according to a comparison example will be explained. In the comparison example, at first, by employing an initial segmentation network, an image segmentation is performed on the prostate on the basis of a medical image. Subsequently, by employing a finish segmentation network, the contour is adjusted in a surrounding region of a prostate contour resulting from the initial segmentation, so as to obtain a final prostate segmentation result.

Figure 7:
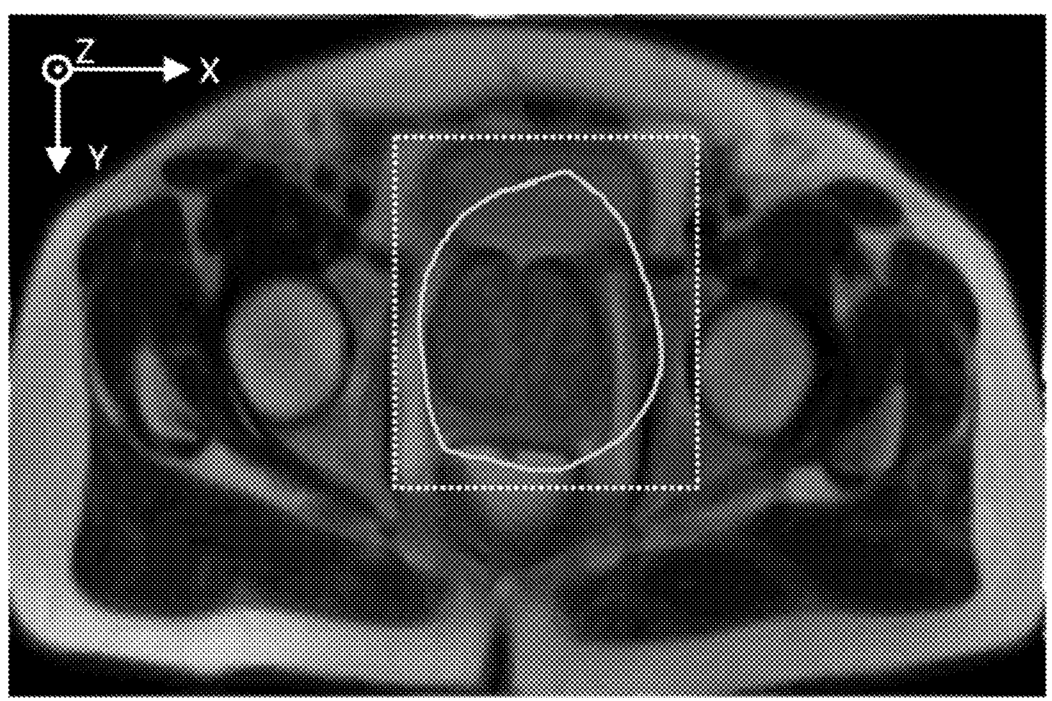
FIG. 7 is a drawing indicating a prostate region specified by using an image segmentation method in a comparison example.

FIG. 7 is a drawing indicating a prostate contour specified by using the image segmentation method in the comparison example. In FIG. 7, the solid line indicates a result of prostate initial segmentation, whereas the dotted line indicates a region in which the segmented contour is present. The comparison example has a problem where because grayscale values of the prostate and the bladder wall are close to each other, the precision level of the initial segmentation for the prostate is low, and the bladder wall can easily be distinguished as the prostate. As illustrated in FIG. 7, the result of the prostate initial segmentation according to the image segmentation method in the comparison example includes a bladder wall region in a large amount, while the region in the initial segmentation result includes invalid regions in a large amount.

Figure 8:
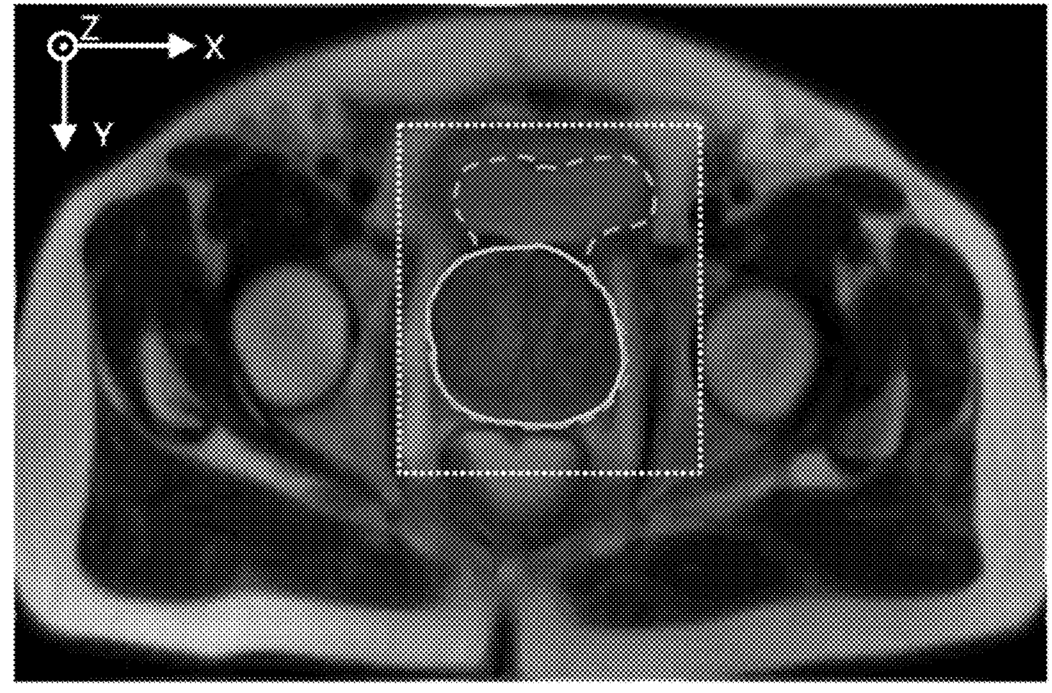
FIG. 8 is a drawing indicating a finish segmentation result according to the image segmentation method in the comparison example.

FIG. 8 is a drawing indicating a finish segmentation result according to the image segmentation method in the comparison example. In FIG. 8, the solid line indicates a result of prostate finish segmentation, while the dashed line indicates the actual prostate contour, whereas the dotted line indicates a region in which the segmented contour is present. In the comparison example, because the contour resulting from the initial segmentation includes the large amount of bladder wall region, the problem remains where the grayscale values of the prostate and the bladder wall at the time of performing the finish segmentation are close to each other, which makes the precision level of the segmentation low. As illustrated in FIG. 8, as a result of the finish segmentation, the contour of the lower part of the prostate is accurately distinguished. However, over-segmentation occurred above the prostate, and a large amount of bladder wall region is included.

Next, advantageous technical effects of the present embodiment will be explained. According to the image segmentation method of the present embodiment, the position of the prostate region is determined by using the plurality of features points. The feature points are not easily impacted by factors such as individual differences among subjects, scans, and facilities and are able to maintain stable and prominent features in medical images. Further, according to the image segmentation method in the present embodiment, the position of the prostate region is determined on the basis of the plurality of feature points of the plurality of types, while taking into account that the stability of the feature points themselves and detection result reliability vary among the different types. It is therefore possible to inhibit errors that may be caused by a detection mistake on a part of the feature points. Thus, reliability of the prostate region position determining process is guaranteed. The prostate region specified according to the image segmentation method of the present embodiment is able to match the actual prostate contour. Consequently, at the time of performing the image segmentation on the segmentation target, it is possible to inhibit over-segmentation caused by the segmentation region being too large or under-segmentation caused by the segmentation region being too small.

Figure 9:
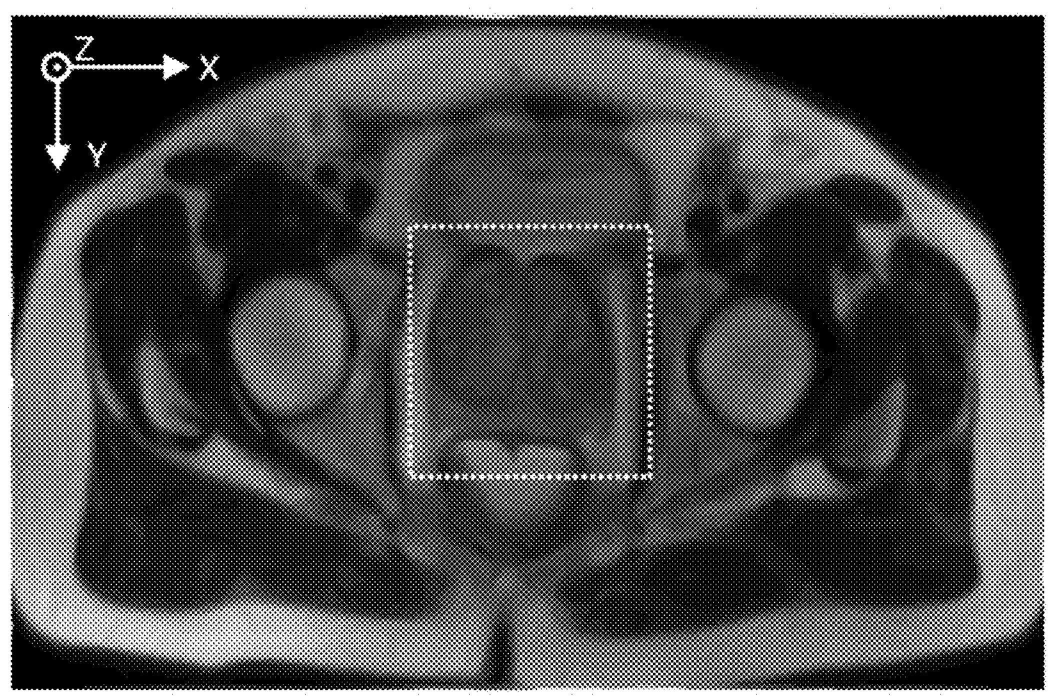
FIG. 9 is a drawing illustrating a prostate region specified by using the image segmentation method according to the present embodiment.

FIG. 9 is a drawing illustrating a prostate region specified by using the image segmentation method according to the present embodiment. In FIG. 9, the dotted line indicates the specified prostate region. In the present embodiment, because the position of the prostate region is determined by using the plurality of feature points, it is possible to accurately determine the position of the prostate region, without having the problem where the prostate region becomes too large.

Figure 10:
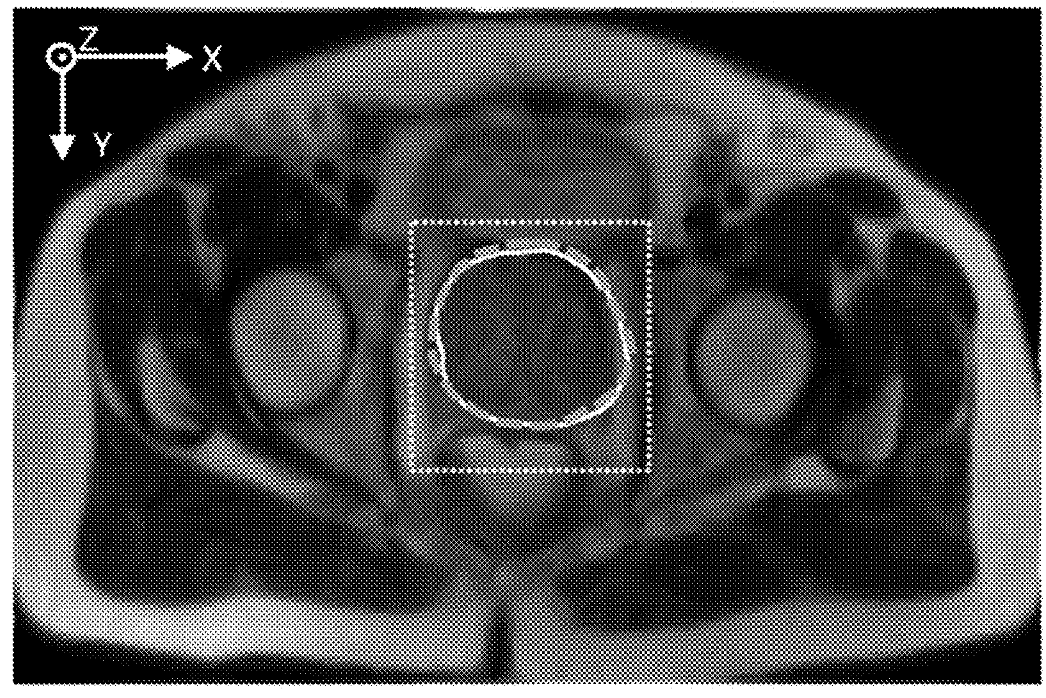
FIG. 10 is a drawing illustrating an image segmentation result according to the image segmentation method in the present embodiment.

FIG. 10 is a drawing illustrating an image segmentation result according to the image segmentation method in the present embodiment. In FIG. 10, the solid line indicates a result of the prostate segmentation, while the dotted line indicates a prostate region, whereas the dashed line indicates the actual prostate contour. In the present embodiment, the specified prostate region tightly surrounds the contour of the prostate, while excluding the region of the bladder wall. Consequently, at the time of performing the image segmentation, even if the neural network model is unable to accurately distinguish the prostate from the bladder wall, it is possible to accurately segment the contour of the prostate and to thus avoid the occurrence of over-segmentation. As illustrated in FIG. 10, in the result of the finish segmentation, the contour of the prostate is accurately distinguished, without having over-segmentation.

By using a segmentation model based on a UNet-2D network, the present inventor verified each of the five data sets having an image size of 256×256 represented by 302 sets of data in total, while using the image segmentation method in the comparison example and the image segmentation method according to the present embodiment. As a result, the Dice index (a set similarity gauging index for measuring similarity between a segmentation result and a true result) of the image segmentation method in the comparison example was 0.86, whereas the Dice index of the image segmentation method according to the present embodiment was 0.92.

In the embodiments described above, the examples were explained in which the image segmentation apparatus and the image segmentation method of the present embodiments are applied to the segmentation of the prostate; however, the image segmentation apparatus and the image segmentation method of the present embodiments are also applicable to other organs and tissues. For example, when the apparatus or the method is applied to segmentation of the pancreas, it is possible to perform the segmentation on the pancreas by selecting a pancreas head, a pancreas tail, and a bottom part of the pancreas head as feature points. The present embodiments are not particularly limited by segmentation targets or corresponding feature points thereof. As explained above, for a specific segmentation target, it is acceptable to select, as the feature points, points that are positioned inside or in the surrounding of the segmentation target, have a prominent anatomical feature, and have a relatively stable relative positional relationship with the segmentation target.

Further, in the embodiment described above, the total reliability degree is calculated by performing the weighted addition on the plurality of feature reliability degrees. However, it is also acceptable to use a sum, an average value, a maximum value, or the like of the plurality of feature reliability degrees, as the total reliability degree.

The term "processor" used in the above explanations denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). The processor is configured to realize the functions by reading and executing the programs saved in a memory. In this situation, instead of having the programs saved in the memory, it is also acceptable to directly incorporate the programs in the circuitry of one or more processors. In that situation, the one or more processors realize the functions by reading and executing the programs incorporated in the circuitry thereof. Further, the processors in the present embodiments do not each necessarily have to be structured as a single piece of circuitry. It is also acceptable to structure one processor by combining together a plurality of pieces of independent circuitry so as to realize the functions thereof.

According to at least one aspect of the embodiments described above, it is possible to perform the image segmentation on the segmentation target easily and precisely, while inhibiting the occurrence of over-segmentation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:

processing circuitry configured to generate, from a medical image, a plurality of feature target regions for determining a target of image segmentation;

calculate, with respect to each position of a plurality of positions in the medical image, a feature reliability degree using, which indicates a probability that the position in the medical image will belong to the target region, for each of the plurality of feature target regions, based on at least one feature point and a feature target region associated with the at least one feature point;

determine a target region indicating the region in which the target of image segmentation is present, based on a plurality of the feature reliability degrees calculated from each of the plurality of feature target regions; and perform, in the target region, the image segmentation on the target.

2. The medical image processing apparatus according to claim 1, wherein the processing circuitry is further configured to:

detect, from the medical image, position information of a plurality of feature points including at least a first feature point and a second feature point;

generate a first feature target region based on the first feature point and generate a second feature target region based on the second feature point; and determine the target region, based on the first feature target region and the second feature target region.

3. The medical image processing apparatus according to claim 2, wherein the processing circuitry is further configured to determine, for each feature point of the first feature point and the second feature point, a position, a shape, and a size of the feature target region associated with the feature point, based on a position of the feature point and relative positions between the feature point and the target.

4. The medical image processing apparatus according to claim 2, wherein for each feature point of the first feature target region and the second feature target region, based on a position reliability coefficient of the feature point and information about the feature target region associated with the feature point, the processing circuitry is further configured to calculate, with respect to each of the positions in the medical image, the feature reliability degree, and the processing circuitry is further configured to calculate, with respect to each of the positions in the medical image, a total reliability degree from a plurality of the feature reliability degrees calculated from each of the first feature target region and the second feature target region, and determine the target region based on the total reliability degrees.

5. The medical image processing apparatus according to claim 4, wherein the processing circuitry is further configured to determine a weight of the feature reliability degree corresponding to the feature point, in accordance with a reliability and a stability of detection of the feature point, and calculate the total reliability degree based on a sum of the plurality of feature reliability degrees to which the weights are applied.

6. The medical image processing apparatus according to claim 2, wherein the target is a prostate, and the plurality of feature points are a pubic bone point, a femur point, a pelvis point, a urethra entrance point, a prostate center point, and a prostate apex point.

7. The medical image processing apparatus according to claim 2, wherein the target is a pancreas, and the plurality of feature points are a head of the pancreas, a tail of the pancreas, and a bottom part of the head of the pancreas.

8. A medical image processing method, comprising:

generating, from a medical image, a plurality of feature target regions for determining a target of image segmentation;

calculating, with respect to each position of a plurality of positions in the medical image, a feature reliability degree, which indicates a probability that the position in the medical image will belong to the target region, for each of using the plurality of feature target regions, based on at least one feature point and a feature target region associated with the at least one feature point;

determining a target region indicating the region in which the target of image segmentation is present, based on a plurality of the feature reliability degrees calculated from each of the plurality of feature target regions; and performing, in the target region, the image segmentation on the target.

* * * * *